United States Patent [19]

Roloff et al.

[11] Patent Number: 4,697,016
[45] Date of Patent: Sep. 29, 1987

[54] INTERMEDIATES FOR THE PREPARATION OF A CARBOXYLIC ACID

[75] Inventors: Achim Roloff, Rheinfelden, Switzerland; Heinz W. Gschwend, New Providence, N.J.

[73] Assignee: Ciba-Geigy Corporation, Ardsley, N.Y.

[21] Appl. No.: 829,336

[22] Filed: Feb. 14, 1986

Related U.S. Application Data

[62] Division of Ser. No. 664,916, Oct. 26, 1984, Pat. No. 4,595,766.

[51] Int. Cl.$^4$ .............. A61K 241/18; A61K 471/04; A61K 487/04; A61K 487/14
[52] U.S. Cl. .................... 544/344; 540/579; 544/349; 544/384
[58] Field of Search ............ 260/243.3; 544/344, 544/349, 385; 540/579

[56] References Cited

U.S. PATENT DOCUMENTS

| | | | |
|---|---|---|---|
| 3,702,321 | 11/1972 | Yamamoto et al. | 260/239 |
| 3,853,878 | 12/1974 | Jonas et al. | 260/268 |
| 3,920,660 | 11/1975 | Fontanella et al. | 250/250 BC |
| 4,140,791 | 2/1979 | Chan | 544/385 |
| 4,374,847 | 2/1983 | Gruenfeld | 548/491 |
| 4,514,568 | 4/1985 | Coates | 544/408 |
| 4,520,205 | 5/1985 | Buzby et al. | 548/491 |

FOREIGN PATENT DOCUMENTS

| | | |
|---|---|---|
| 1340528 | 12/1973 | United Kingdom . |
| 1340529 | 12/1973 | United Kingdom . |

OTHER PUBLICATIONS

A. Padwa (Editor), Organic Photochemistry, vol. 6, (1983), pp. 16, 17, 26, 32 and 38, Dekker Inc. NY, AD6-01A1.
Schultz, et al., Synthesis of Functionalized, Indolines, Tetrahedron 36, 1757 (1980).
Bycroft et al., Asymmetric Synthesis of α-Amino Acids, JCS Chem. Comm. 1975, 988.
Stanton et al., J. Med. Chem., 26, 1267 (1983), Bicycl Acid Derivatives.
Yoshimara et al., Bull. Chem. Soc. Japan, 46,2850–2853 (1973).
Official Gazette Abstract for U.S. Pat. No. 4,485,241, (Nov. 27, 1984).

*Primary Examiner*—Mark L. Berch
*Attorney, Agent, or Firm*—Norbert Gruenfeld

[57] ABSTRACT

The invention relates to a novel process for the preparation of the optically pure 2S- or 2R-indolinecarboxylic acid of the formula

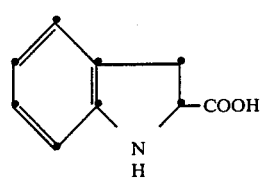

I and salts thereof. The process comprises forming the heterocyclic 5-membered ring in formula I from an open chain precursor by diastereoselective cyclization.

7 Claims, No Drawings

INTERMEDIATES FOR THE PREPARATION OF A CARBOXYLIC ACID

This is a divisional of application Ser. No. 664,916 filed on Oct. 26, 1984 now U.S. Pat. No. 4,595,766.

The present invention relates to a novel process for the preparation of the optically pure 2S- or 2R-indolinecarboxylic acid of the formula

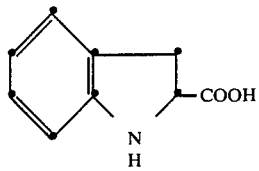

and salts thereof. This chiral heterocycle is an important synthesis building block for the manufacture of a number of pharmacologically very valuable compounds, for example 1-(4-ethoxycarbonyl-2R,4R-dimethylbutanoyl)-2S-indolinecarboxylic acid, q.v. for example EP-A No. 0 050 850. This publication describes the preparation of highly effective ACE inhibitors using compounds of formula I. Up to now it has only been possible to prepare the enantiomers of formula I by resolving racemic mixtures and accepting the drawbacks inherent in such separating methods. The process of the present invention avoids the drawbacks of resolving a racemic mixture, in particular the loss of substance involved in the separation. The stereochemically uniform orientation at the C2 atom of a compound of the formula I is achieved in this invention by forming the heterocyclic 5-membered ring in the formula I from an open chain precursor by diastereoselective cyclisation.

Specifically, the present invention relates to a process for the preparation of the optically pure compound of formula I and salts thereof, which comprises diastereoselectively cyclising a compound of the formula

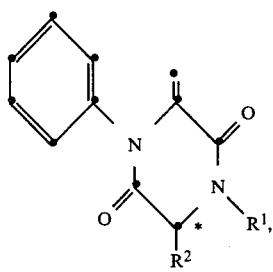

wherein $R^1$ is hydrogen, lower alkyl or aryl-lower alkyl, $R^2$ is lower alkyl or lower alkyl which is substituted by lower alkoxy, lower alkylthio, aryl or lower alkoxyaryl, or is aryl, or wherein $R^1$ and $R^2$, when taken together, are lower alkylene which may be substituted by lower alkoxy or fused to a 5- to 7-membered carbocyclic ring, and wherein the symbol * denotes a carbon atom which is always either in the S or in the R configuration, to give a compound of the formula

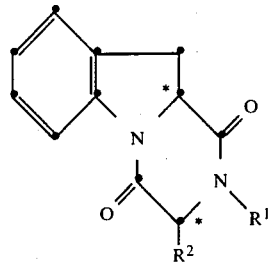

wherein $R^1$ and $R^2$ have the given meanings and each symbol * denotes a carbon atom, with both carbon atoms together being either in the S configuration or in the R configuration, hydrolysing said compound and isolating the compound of formula I, optionally in the form of a salt, from the hydrolysate, and, if desired, converting a resultant free compound of the formula I into a salt or converting a salt into another salt or into the free compound of the formula I.

Unless otherwise defined, the general terms employed throughout this specification have the meanings given below. The term "lower" will be understood as meaning that the groups or compounds so qualified contain 1 to 7, preferably 1 to 4, carbon atoms.

Lower alkyl is for example methyl, ethyl, n-propyl, isopropyl, n-butyl, 2-butyl, isobutyl or tert-butyl, and also n-pentyl, n-hexyl or n-heptyl.

Lower alkoxy is preferably methoxy, ethoxy, n-propoxy, isopropoxy, n-butoxy, isobutoxy or tert-butoxy. Lower alkylthio is e.g. methylthio or ethylthio.

Aryl by itself or as moiety of another substituent, e.g. aryl-lower alkyl, denotes an aromatic hydrocarbon radical and is e.g. 1-or 2-naphthyl, but is preferably phenyl. Phenyl-lower alkyl is e.g. benzyl or 1- or 2-phenylethyl. Lower alkoxyaryl is e.g. lower alkoxyphenyl and is preferably 2-, 3- or 4-methoxyphenyl.

Lower alkylene is preferably $C_2$-$C_6$alkylene and is e.g. 1,2-ethylene, 1,2- or 1,3-propylene, 1,3- or 1,4-butylene, 1,5-pentylene or 1,6-hexylene, so that $R^2$—CH—N—$R^1$ grouping forms e.g. the pyrrolidine ring.

Lower alkoxy-substituted lower alkylene is preferably substituted at those carbon atoms which are not attached to nitrogen and is for example 2-methoxy-1,3-propylene.

Lower alkylene which is fused to a 5- to 7-membered carbocyclic ring is preferably $C_2$-$C_6$alkylene which is fused to a saturated, partly saturated or aromatic carbocyclic ring, for example to cyclopentyl, cyclohexyl, cycloheptyl, cyclohexenyl or phenyl, so that the $R^2$—CH—N—$R^1$ grouping forms e.g. the indoline ring.

Salts are for example therapeutically useful salts such as metal or ammonium salts of the acid of formula I, in particular alkali metal or alkaline earth metal salts, e.g. sodium, potassium, magnesium or calcium salts, preferably readily crystallising ammonium salts. These salts are derived from ammonia or from organic amines, e.g. mono-, di- or tri-lower alkylamines, mono-, di- or tri-lower cycloalkylamines or mono-, di- or tri-lower hydroxyalkylamines, lower alkylenediamines or hydroxy-lower alkyl-lower alkylammonium bases or aryl-lower alkyl-lower alkylammonium bases, e.g. methylamine, diethylamine, triethylamine, dicyclohexylamine, triethanolamine, ethylenediamine, tris(hydroxymethyl)aminomethane or benzyltrimethylammonium hydroxide. The compound of formula I also forms acid addition salts. Such salts are prepared e.g. from those acids which afford therapeutically useful acid addition salts, e.g. inorganic acids such as hydrohalic acids, for example hydrochloric or hydrobromic acid, or sulfuric, phosphoric, nitric or perchloric acid; or preferably organic acids such as aliphatic or aromatic carboxylic or sulfonic acids, for example formic acid, acetic acid, propionic acid, succinic acid, glycolic acid, lactic acid, malic acid, tartaric acid, citric acid, maleic acid, fumaric acid, hydroxymaleic acid, pyruvic acid, phenylacetic acid, benzoic acid, 4-aminobenzoic acid, anthranilic acid, 4-hydroxybenzoic acid, salicylic acid, 4-aminosalicylic, pamoic acid, nicotinic acid, methanesulfonic acid, ethanesulfonic acid, hydroxyethanesulfonic acid, ethylenesulfonic acid, halobenzenesulfonic acid, toluenesulfonic acid, naphthalenesulfonic acid, sulfanilic acid or cyclohexylsulfamic acid; or ascorbic acid. Pharmaceutically unsuitable salts, for example picrates, also fall within the scope of this invention.

In particular, the present invention relates to a process for the preparation of compounds of the formula I and salts thereof, which comprises starting from a compound of the formula II, wherein $R^1$ is hydrogen, lower alkyl or phenyl-lower alkyl, $R^2$ is lower alkyl or lower alkyl which is substituted by lower alkoxy, lower alkylthio, aryl or lower alkoxyaryl, or is aryl, or wherein $R^1$ and $R^2$, when taken together, are $C_3$-$C_4$alkylene which may be substituted by lower alkoxy or fused to a 5- to 7-membered carbocyclic ring, and wherein the symbol * denotes a carbon atom which is always either in the S or in the R configuration.

The invention relates more particularly to a process for the preparation of compounds of formula I and salts thereof, which comprises starting from a compound of the formula II, wherein $R^1$ is hydrogen, methyl or benzyl, and $R^2$ is lower alkyl or phenyl, or wherein $R^1$ and $R^2$, when taken together, are 1,3-propylene which may be fused to a 5- or 6-membered carbocyclic ring and wherein the symbol * denotes a carbon atom which is always either in the S or in the R configuration.

Most particularly, the invention relates to a process for the preparation of compounds of formula I and salts thereof, which comprises starting from a compound of the formula II, wherein the $R^2$—CH—N—$R^1$ grouping denotes the S- or R- pyrrolidine ring or the S- or R- indoline ring. In this process, it is preferred to use those starting compounds of the formula II in which the carbon atom carrying the radical $R^2$ is the S configuration.

The process of this invention can be considered as a cyclisation reaction (formation of III from II) and a hydrolysis (formation of I from III). The process steps are carried out as follows in a manner known per se.

CYCLISATION

A 3-methylene-2,5-diketopiperazine of the formula II is cyclised photochemically in an inert solvent, preferably in an inert gas atmosphere. Examples of suitable inert solvents are: hydrocarbons such as hexane, toluene or, preferably, benzene; halogenated hydrocarbons such as chloroform or dichloromethane; lower alkanecarbonitriles such as acetonitrile, or lower alkanols such as methanol, ethanol or, preferably, tert-butanol. Suitable inert gases are for example argon or nitrogen. Photochemical energy is conveniently supplied by a medium pressure mercury lamp or xenon arc-lamp, using for laboratory conditions for example a Philips HPK 125 watt lamp, an Osram XBO 450 watt lamp or an Ace-Hanovia 450 watt lamp. The process can be carried out either by direct irradiation or be sensitized by conventional triplet sensitisers. For reacting e.g. 0.01 to 0.1 mole, the reaction times are from about ¼ hour to 72 hours. Depending on the solvent employed, the reaction temperature is in the range from 0° to 80° C. The batch may be cooled to prevent overheating. Depending on the size of the batches, it is also possible to use stronger sources of energy.

HYDROLYSIS

A compound of the formula III obtained by cyclisation as described above is cleaved by hydrolysis of both amide groups of the diketopiperazine into the desired compound of the formula I and into the readily separable amino acid of the formula

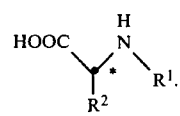

The hydrolysis is effected in the manner conventionally employed for amide hydrolyses [q.v. for example Tetrahedron Letters 46, 4483 (1979)], preferably by treatment with a strong acid such as a hydrohalic acid, for example hydrochloric acid, at elevated temperature, e.g. from 80° to 150° C. The separation of the two amino acids I and IV can be carried out by appropriate conventional separating methods, for example by chromatographic separating methods.

Depending on the process conditions, the compound of the formula I can be obtained as free compound in the form of an inner salt, as it is an amino acid, or as a metal or ammonium salt or as an acid addition salt. The conversions of the free compound of the formula I into a salt or of a salt into another salt or into the free compound of the formula I, can be carried out in a manner known per se.

In a particularly preferred process variant, the $R^2$—CH—N—$R^1$ grouping in the formulae II, III and IV denotes the 2S- or 2R-pyrrolidine ring or the 2S- or 2R-indoline ring. In these two last mentioned cases, the hydrolysis of the compound of formula III gives two equivalents of the compound of formula I, as formulae I and IV are then identical. Separation of the hydrolysate IV from I—necessary in all other cases—is consequently here unnecessary.

The process also comprises those embodiments wherein intermediates are isolated and the remaining process steps are carried out therewith, or wherein the starting materials are prepared in situ and used without being isolated, or wherein the process is discontinued at any stage. Starting materials can also be used in the form of derivatives or formed during the reaction.

The starting compounds of the formula II are novel and constitute a further object of the present invention. The same definitions of $R^1$, $R^2$ and the symbol * apply, especially those definitions highlighted as "in particular", "more particularly" and "most particularly".

The intermediates of the formula III are also novel, except the cyclodipeptide of the indoline carboxylic acid, and to this extent constitute a further object of the invention. The definitions of $R^1$, $R^2$ and the symbol * likewise apply here, especially also those definitions highlighted as "in particular", "more particularly" and "most particularly".

The compounds of the formula II can be obtained in a manner known per se, for example by condensing an amino acid anilide of the formula V with pyruvic acid of the formula VI, in the presence of thionyl chloride in dimethylformamide, and dehydrating the condensate so obtained. It is probable that the compounds of the formulae VII and VIII will be formed in this reaction, but they do not need to be isolated. Amino acid anilides of the formula V are obtainable in conventional manner from amino acids of the formula IV, which can be recycled in this manner, and from aniline.

In the compounds of formulae V, VII and VIII, the symbols $R^1$, $R^2$ and * are as defined for formula II.

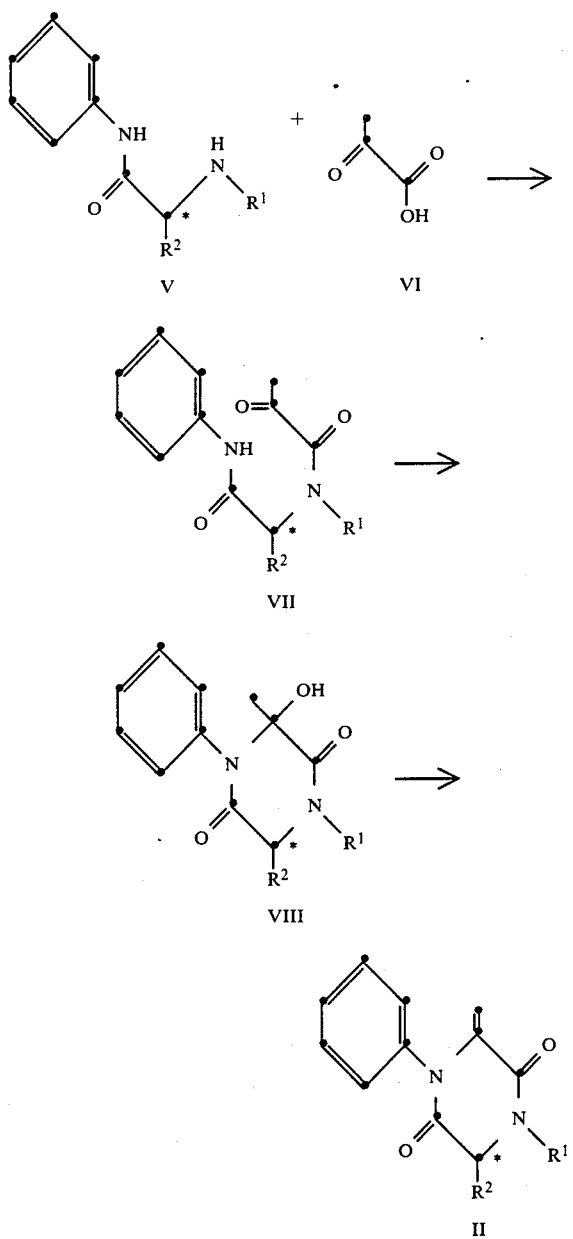

An alternative procedure for obtaining compounds of the formula II comprises condensing pyruvic acid of the formula VI with an amino acid of the formula IV and subsequently cyclising the condensate with aniline to give a compound of the formula VIII. Such reactions affording starting compounds of the formula II belong to the state of the art and therefore require no further explanation.

The following Examples illustrate the invention without implying any restriction to what is described therein.

EXAMPLE 1

2.42 g of 3-methylene-2-phenyl-2,3,6,7,8,8a-hexahydropyrrolo[1,2-a]-[8aS]-pyrazine-1,4-dione are irradiated for 24 hours at room temperature in 1000 ml of tert-butanol with a medium pressure mercury lamp (Philips HPK 125 watt). The solvent is distilled off and the residue is recrystallised from dichloromethane/diethyl ether (1:1) to give pale crystals of the cyclodipeptide of S-proline and 2S-indolinecarboxylic acid. Melting point: 153° C., $[\alpha]_{365\ nm} = -107°$ (c=1 in ethanol).

1.2 g of the above cyclodipeptide are heated in 6M HCl for 12 hours at 110° C. The cooled solution is then neutralised with triethylamine and extracted with chloroform. The organic phase is concentrated by evaporation and the residue is chromatographed through a column of silica gel eluted with tert-butanol/water/acetic acid (4:1:1). The fractions which exclusively contain material with an $R_f$-value of 0.47 are concentrated to give pure 2S-indolinecarboxylic acid with a melting point of 175° C.; $[\alpha]_D^{20} = -114°$ (c=1 in 2N HCl).

The starting material of the formula II employed is prepared as follows:

17.6 g of pyruvic acid in 30 ml of dimethylformamide are cooled to 10° C. and, at this temperature, 23.8 g of thionyl chloride are added over 20 minutes. The orange solution is stirred for 1 hour at 10° C. and then a solution of 19.0 g of S-proline anilide and 80 ml of dichloromethane is added over 5 minutes. Despite cooling with ice, the temperature rises to about 20° C. The dark red solution is cooled to 0°-5° C. and then a solution of 20.2 g of triethylamine and 15 ml of dichloromethane is added dropwise. Stirring is then continued for 2 hours at room temperature. The brownish red solution is concentrated in a rotary evaporator at a bath temperature of 70° C. and the residue is taken up in 100 ml of water and 200 ml of dichloromethane. The organic phase is washed with 2×50 ml of water and 100 ml of sodium chloride solution and the organic phase is concentrated by evaporation and dried. The crude crystalline product is dissolved in 200 ml of hot methanol and the solution is clarified with 3 g of activated charcoal, filtered over kieselguhr (Hyflo) and cooled. Repeated recrystallisation of the resultant crystals from dichloromethane/diethyl ether (1:1) yields 3-methylene-2-phenyl-2,3,6,7,8,8a-hexahydropyrrolo[1,2-a]-[8aS]-pyrazine-1,4-dione with a melting point of 186° C.; $[\alpha]_{365\ nm} = -82°$ (c=1, ethanol).

EXAMPLE 2

To 0.87 g of 3-methylene-2-phenyl-2,3,10,10a-tetrahydropyrazino[1,2-a]-[10aS]-indole-1,4-dione are added 350 ml of tert-butanol and 35 ml of dimethylformamide. The suspension is blanketed with argon for 30 minutes and then irradiated for 24 hours with a medium pressure mercury lamp (Philip HPK 125 watt lamp) in a quartz apparatus. The solvent is distilled off to give light brown crystals. Purification through a column of silica gel eluted with ethyl acetate/toluene (1:1) yields the cyclodipeptide of 2S-indolinecarboxylic acid as a pale crystalline solid with a melting point of 261°–263° C.

0.5 g of the above cyclodipeptide are heated in 10 ml of 6N hydrochloric acid for 15 hours to 110° C. The mixture is cooled and then neutralised with 2N aqueous sodium hydroxide solution and the aqueous phase is extracted with dichloromethane. The organic phase is separated and concentrated by evaporation, affording 2S-indolinecarboxylic acid as a pale crystalline solid. Melting point: 173°–175° C.; $[\alpha]_D^{20} = -113°$ (c = 1 in 2N HCl).

The starting material of the formula II employed is prepared as follows:

16.3 of 2S-indolinecarboxylic acid are added to 50 ml of water and then about 25 ml of 4N aqueous sodium hydroxide solution are added to bring the pH of the solution to 9.5. The solution is cooled to 0° C. and benzyl chloroformate is added dropwise over 30 minutes, while keeping the pH constant by appropriate addition of aqueous sodium hydroxide solution. When the dropwise addition is complete, the mixture is stirred for 5 hours at 0° C. The suspension is warmed to room temperature and the aqueous phase is extracted with ether. The aqueous phase is then added to a mixture of 200 g of ice, 40 ml of concentrated hydrochloric acid and 60 ml of water. The precipitated product is taken up in chloroform and the solution is dried. Recrystallisation from ether/petroleum ether (b.p. 40°–60° C.) yields 1-benzyloxycarbonyl-2S-indolinecarboxylic acid with a melting point of 116° C.

18.6 g of 1-benzyloxycarbonyl-2S-indolinecarboxylic acid are dissolved in 200 ml of ethyl acetate and the solution is cooled to −20° C. To this solution are added 6.32 g of N-methylmorpholine and then 6.87 g of ethyl chloroformate are added dropwise such that the temperature does not rise above −15° C. 5.86 g of aniline are added dropwise to the suspension obtained above at −20° C. and the mixture is warmed to room temperature and stirred for 1 hour. The suspension is filtered and the filter residue is washed with water and dried, affording 1-benzyloxycarbonyl-2S-indolinecarboxylic acid anilide with a melting point of 222° C.

5 g of 1-benzyloxycarbonyl-2S-indolinecarboxylic acid anilide are dissolved in 100 ml of dimethylformamide and to this solution is added 1 g of palladium catalyst (5% Pd on activated carbon). The mixture is hydrogenated with hydrogen in a shaking flask at room temperature and under normal pressure. After 6 minutes the hydrogen absorption is 98% and the hydrogenation has ceased. The catalyst is removed by filtration and the solution is concentrated by evaporation and the residue is purified through a column of silica gel eluted with toluene/ethyl acetate. The eluate is concentrated to give 2S-indolinecarboxylic acid anilide with a melting point of 110° C.

While cooling with ice, 10 ml of dimethylformamide are added to 4.4 g of pyruvic acid. Then 6.3 g of thionyl chloride are added dropwise at 0°–5° C. and the mixture is stirred for 30 minutes in an ice-bath. A solution of 5.95 g of 2S-indolinecarboxylic acid anilide in 20 ml of dichloromethane is added dropwise to the above solution and the mixture is stirred for 2 hours. Then a solution of 5.5 g of triethylamine in 5 ml of dichloromethane is added such that the temperature of the reaction mixture does not rise above +5° C. The brown suspension is stirred for 30 minutes and then filtered. The filter residue is washed with 20 ml of ether and the filtrate is concentrated at a bath temperature of 80° C. The crystalline residue is washed with 50 ml of ethyl acetate and 50 ml of ether and dried in vacuo, affording white crystals of 3-methylene-2phenyl-2,3,10,10a-tetrahydropyrazino[1,2-a]-[10aS]-indole-1,4-dione with a melting point of 241°–243° C.

EXAMPLE 3

0.8 g of 3,4-dimethyl-6-methylene-1-phenyl-(3S)-piperazine-2,5-dione are dissolved in 350 ml of tert-butanol and the solution is irradiated for 24 hours with a Philips HPK 125 medium pressure mercury lamp. The solvent is evaporated off in vacuo, affording 2,3-dimethyl-2,3,10,10a-tetrahydropryazino[1,2-a]-[3S,10aS]-indole-1,4-dione, 250 MHz NMR (CDCl$_3$, data: δ in ppm, multiplicity, number of protons): 1.6 (d, 3H); 3.08 (s, 3H); 3.4–3.6 (m, 2H); 4.0 (q, 1H); 4.8 (t, 1H); 7.1–7.3 (m, 3H); 8.05 (dd, 1H); $[\alpha]_D = +20.1°$ (c = 1, ethanol).

The hydrolysis of 2,3-dimethyl-2,3,10,10a-tetrahydropyrazino[1,2-a]-[3S,10aS]-indole-1,4-indole to give the S-enantiomer of the formula I is carried out in accordance with Example 1.

The required starting material of the formula II can be obtained as follows:

N-benzyloxycarbonyl-N-methyl-S-alanine anilide of m.p. 65° C. is prepared by a procedure analogous to that for obtaining the starting material in Example 2. The N-methyl-S-alanine anilide of m.p. 42° C. can in turn be prepared therefrom in analogous manner.

5.28 g of pyruvic acid are dissolved in 10 ml of dimethylformamide and to this solution are added 4.4 ml of thionyl chloride at −15° C. The yellow solution is stirred for 30 minutes while cooling with ice and then a solution of 5.5 g N-methyl-S-alanine anilide in 20 ml of dichloromethane is added. The brown suspension so obtained is stirred for 2 hours and 8.3 ml of triethylamine are than added at 0° C. The mixture is concentrated by evaporation at a bath temperature of 80° C. and the residue is taken up in 150 ml chloroform. The solution is washed with three 50 ml portions of water. The organic phase is dried and purified over silica gel eluted wih toluene/ethyl acetate (1:1), affording 3,4-dimethyl-6-methylene-1-phenyl-3S-piperazine-2,5-dione as a viscous oil. 250 MHz NMR (CDCl$_3$, data: δ in ppm, multiplicity, number of protons): 1.66 (d, 3H); 3.1 (s, 3H); 4.15 (q, 1H); 4.64 (s, 1H); 5.76 (s, 1H), 7.1–7.3 (m, 2H); 7.6–7.8 (m, 3H); $[\alpha]_D = -29.7°$ (c = 1, ethanol).

EXAMPLE 4

2.42 g of 3-methylene-2-phenyl-2,3,6,7,8,8a-hexahydropyrrolo[1,2-a]-[8aR]-pyrazine-1,4-dione are irradiated for 24 hours with a medium pressure mercury lamp in 1 l of tert-butanol at room temperature under nitrogen (Philips HPK 125 watt lamp). The solvent is stripped off and the residue is recrystallised from dichloromethane/diethyl ether (1:1) to give the cyclodipeptide of R-proline and 2R-indolinecarboxylic acid as a pale crystalline solid with a melting point of 151°–153° C.; $[\alpha]_{365\ nm} = +105°$ (c = 1, ethanol).

1.5 g of the above cyclodipeptide are boiled overnight in 20 ml of 6N HCl at 110° C. The solution is cooled and then neutralised with triethylamine and the aqueous phase is filtered. The filtrate is extracted with 50 ml of dichloromethane and the organic phase is concentrated by evaporation. Separation over 50 g of silica gel eluted with butanol/glacial acetic acid/water (4:1:1) yields 2R-indolinecarboxylic acid. $R_f = 0.47$ (R-proline: $R_f = 0.08$); m.p. 174°–175° C.; $[\alpha]_D^{20} = +112°$ (c = 1 in 2N HCl).

The starting material of the formula II employed can be prepared as follows:

4.4 of pyruvic acid are dissolved in 10 ml of dimethylformamide. The solution is cooled to 10° C. and then 5.5 g of thionyl chloride are added. The pale red solution is stirred for 1 hour at 10° C. and then a solution of 4.7 g of R-proline anilide in 20 ml of dichloromethane is added. Despite cooling, the temperature rises to about 15° C. After cooling to 0°–5° C., a solution of 5.05 g of triethylamine in 5 ml of dichloromethane is added dropwise and the mixture is stirred for 2 hours at room temperature. The brownish red mixture is concentrated by evaporation in a rotary evaporator at a bath temperature of 70° C. and the residue is taken up in 25 ml of water and 50 ml of dichloromethane. The organic phase is washed twice with 20 ml of water and 20 ml of a concentrated solution of sodium chloride, then concentrated by evaporation and dried. The crude crystalline product is dissolved in 50 ml of boiling methanol and the solution is treated with 0.5 g of activated carbon and filtered, affording 3-methylene-2-phenyl-2,3,6,7,8,8a-hexahydropyrrolo[1,2-a]-[8aR]-pyrazine-1,4-dione as pale crystals with a melting point of 184°–185° C.; $[\alpha]_{365\ nm} = +81°$ (c=1 in ethanol).

What is claimed is:

1. A compound of the formula

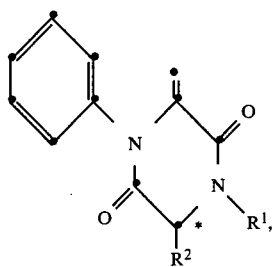

wherein $R^1$ is hydrogen, lower alkyl or aryl-lower alkyl, $R^2$ is lower alkyl or lower alkyl which is substituted by lower alkoxy, lower alkylthio, aryl or lower alkoxyaryl, or is aryl, or wherein $R^1$ and $R^2$, when taken together, are $C_2$–$C_6$ alkylene which may be substituted by lower alkoxy or fused to a 5- to 7-membered saturated, partly saturated or aromatic carbocyclic ring, and wherein the symbol * denotes a carbon atom which is either in the S or in the R configuration.

2. A compound according to claim 1 of the formula

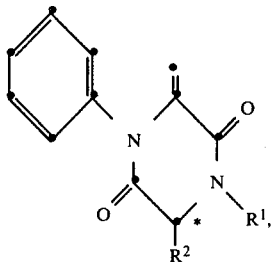

wherein $R_1$ is hydrogen, lower alkyl or phenyl-lower alkyl, $R^2$ is lower alkyl or lower alkyl which is substituted by lower alkoxy, lower alkylthio, phenyl or lower alkoxyphenyl, or is phenyl, or wherein $R^1$ and $R^2$, when taken together, are $C_3$–$C_4$ alkylene which may be substituted by lower alkoxy or fused to a 5- to 7-membered carbocyclic ring selected from cyclopentyl, cyclohexyl, cycloheptyl, cylohexenyl or phenyl, and wherein the symbol * denotes a carbon atom which is either in the S or in the R configuration.

3. A compound of the formula II according to claim 2, wherein $R^1$ is hydrogen, methyl or benzyl, and $R^2$ is lower alkyl or phenyl, or wherein $R^1$ and $R^2$, when taken together, are 1,3-propylene which may be fused to a 5- or 6-membered carbocyclic ring selected from cyclopentyl, cyclohexyl, cyclohexenyl or phenyl, and wherein the symbol * denotes a carbon atom which is always either in the S or in the R configuration.

4. A compound of the formula II according to claim 2, wherein the $R^2$—CH—N—$R^1$ grouping denotes the S- or R-pyrrolidine ring or the S- or R-indoline ring.

5. A compound of claim 2 being S- or R-3-methylene-2-phenyl-2,3,6,7,8,8a-hexahydropyrrolo[1,2-a]-pyrazine-1,4-dione.

6. A compound of claim 2 being S- or R-3-methylene-2-phenyl-2,3,10,10a-tetrahydropyrazino[1,2-a]-indole-1,4-dione.

7. A compound of claim 2 being S- or R-3,4-dimethyl-6-methylene-1-phenyl-piperazine-2,5-dione.

* * * * *